United States Patent
Tsai et al.

(10) Patent No.: US 6,838,403 B2
(45) Date of Patent: Jan. 4, 2005

(54) BREATHABLE, BIODEGRADABLE/COMPOSTABLE LAMINATES

(75) Inventors: Fu-Jya Daniel Tsai, Appleton, WI (US); Bridget A. Balogh, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/752,017

(22) Filed: Dec. 28, 2000

(65) Prior Publication Data

US 2002/0123290 A1 Sep. 5, 2002

(51) Int. Cl.⁷ .............................................. B32B 27/12
(52) U.S. Cl. ...................... 442/394; 442/414; 442/395; 442/398; 428/913; 156/229
(58) Field of Search ................................ 442/394, 414, 442/398, 395; 428/913; 156/229

(56) References Cited

U.S. PATENT DOCUMENTS 5,407,979 A * 4/1995 Wu et al. ...................... 524/47
5,783,504 A   7/1998 Ehret et al.
5,851,937 A * 12/1998 Wu et al. .................... 156/229

FOREIGN PATENT DOCUMENTS

| GB | 2 243 327 A | 10/1991 |
| JP | 11048436 A * | 2/1999 |
| WO | WO 97/29909 A | 8/1997 |
| WO | WO 01/19592 A | 3/2001 |
| WO | WO 02/42365 A | 5/2002 |

OTHER PUBLICATIONS

Patent Abstracts of Japan, vol. 1998, No. 03, Feb. 27, 1998, JP 09–291164 A (Mitsubishi Chem. Corp.) Nov. 11, 1997, abstract.

Patent Abstracts of Japan, vol. 1997, No. 03, Mar. 31, 1997, JP 08–295748 A (Daicel Chem. Ind. Ltd.) Nov. 12, 1996, abstract.

* cited by examiner

*Primary Examiner*—Elizabeth M. Cole
(74) *Attorney, Agent, or Firm*—Brinks Hofer Gilson & Lione

(57) ABSTRACT

A breathable, biodegradable/compostable laminate for use in personal care products. The laminates may be produced from polymer blends. The biodegradable/compostable laminates may be used in a disposable absorbent product intended for the absorption of fluids such as body fluids.

14 Claims, No Drawings

BREATHABLE, BIODEGRADABLE/COMPOSTABLE LAMINATES

FIELD OF THE INVENTION

The present invention relates to breathable, biodegradable/compostable laminates for personal care products. The laminates may be produced from polymer blends. The biodegradable/compostable laminates may be used in a disposable absorbent product intended for the absorption of fluids such as body fluids.

BACKGROUND OF THE INVENTION

The development of environmentally friendly personal care products is very important in today's society. Environmentally friendly personal care products are not only desired to meet the needs of environmentally conscious consumers, they will likely be required by law in the future. Current personal care products are made from a combination of pulp, super-absorbents, elastomers, film, adhesives, and nonwoven components. The films and nonwovens are comprised mainly of polyolefins including polypropylene and polyethylene. After use, products are placed in landfills where they do not appreciably degrade over time. Though this type of landfill disposable is acceptable now, it is likely that landfill space will become scarce in the future and regulations will be created to limit the amount of products to be disposed of in this way. In Europe and Asia, where space is significantly limited compared to the U.S., regulations are already in development. In view of this, it is important to develop personal care products that degrade after use.

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a liquid-permeable topsheet, a fluid acquisition layer, an absorbent structure, and a liquid-impermeable backsheet. These products usually include some type of fastening system for fitting the product onto the wearer.

Disposable absorbent products are typically subjected to one or more liquid insults, such as of water, urine, menses, or blood, during use. As such, the outer cover materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable baby diapers and other disposable absorbent products have been generally accepted by the public, these products still have need of improvement in specific areas. For example, many disposable absorbent products can be difficult to dispose of. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way. If the outer cover materials are made very thin in order to reduce the overall bulk of the disposable absorbent product so as to reduce the likelihood of blockage of a toilet or a sewage pipe, then the outer cover material typically will not exhibit sufficient strength to prevent tearing or ripping as the outer cover material is subjected to the stresses of normal use by a wearer.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that can be disposed of by means other than by incorporation into solid waste disposal facilities such as landfills.

As such, there is a need for new materials that may be used in disposable absorbent products that generally retain their integrity and strength during use, but after such use, the materials may be more efficiently disposed of. For example, the disposable absorbent product may be easily and efficiently disposed of by composting. Alternatively, the disposable absorbent product may be easily and efficiently disposed of to a liquid sewage system wherein the disposable absorbent product is capable of being degraded.

Although degradable monocomponent fibers are known, problems have been encountered with their use. In particular, known degradable fibers typically do not have good thermal dimensional stability such that the fibers usually undergo severe heat-shrinkage due to the polymer chain relaxation during downstream heat treatment processes such as thermal bonding or lamination.

In contrast, polyolefin materials, such as polypropylene, typically exhibit good thermal dimensional stability but also have problems associated with their use. In particular, polyolefin fibers typically are hydrophobic and, and such, exhibit poor wettability, thus limiting their use in disposable absorbent products intended for the absorption of fluids such as body fluids. Although surfactants can be used to improve the wettability of polyolefin fibers, the use of such surfactants introduces additional problems such as added cost, fugitivity or permanence, and toxicity. Furthermore, polyolefin fibers are generally not biodisintegratable or compostable.

Additionally, breathability is an important aspect for personal care articles. For example, breathability in a diaper provides significant skin health benefits to the baby wearing the diaper. Moisture vapors are allowed to pass through the outer cover, leaving the baby's skin drier and less prone to diaper rash.

It would therefore be desirable to prepare a breathable, biodegradable/compostable laminates for personal care products. The biodegradable/compostable laminates may be used in a disposable absorbent product intended for the absorption of fluids such as body fluids.

SUMMARY OF THE INVENTION

The present invention is directed to a breathable, biodegradable/compostable laminate material that is substantially biodegradable and yet which is easily prepared and readily processable into desired final structures. A material is considered biodegradable/compostable if it degrades from the action of naturally occurring microorganisms, such as bacteria, fungi or algae. Biodegradable compostability may be determined using a variety of different test methods. One such test method is ASTM Test Method 5338.92.

One aspect of the present invention concerns a breathable, biodegradable/compostable laminate material that includes an aliphatic polyester polymer and a filler material.

One embodiment of such an aliphatic polyester polymer includes polybutylene succinate (PBS), while another embodiment includes polybutylene succinate adipate copolymers (PBSA).

The laminate materials of the present invention are desirably used as an outer cover for a personal care product. The laminates are designed to include a majority (i.e. ≧50%, weight basis) of biodegradable materials. Additionally, these materials are highly breathable, which makes the materials more comfortable to the wearer of the laminate. Finally, the laminates are relatively simple to produce as they are composed of two layers, a first biodegradable nonwoven material and a second biodegradable film having a filler material.

Since these laminates are simple, two-layer structures, they may be made by a variety of processes, such as thermal bonding, adhesive bonding, or extrusion lamination.

The laminate materials of the present invention are useful in a wide variety of personal care articles, such as diapers, adult incontinence products, training pants, and feminine care products, among others.

DETAILED DESCRIPTION OF THE INVENTION

The present invention is directed to a breathable, biodegradable/compostable laminate material that is substantially biodegradable and yet which is easily prepared and readily processable into desired final structures. The laminates may be made from a variety of biodegradable polymers, organic and inorganic fillers, and by a number of film or laminate forming processes. These laminates provide a film that is comfortable to wear, yet will biodegrade or compost, thereby reducing the burden of disposing of the final structure, such as a personal care article.

The present invention is also directed to methods of forming a breathable, biodegradable/compostable laminate material that is substantially biodegradable. The methods include the laminating of two layers to form the laminate material of the present invention. The two layers include a biodegradable nonwoven material and a filled, biodegradable film and they may be laminated using a variety of different lamination processes.

The present invention provides a laminate material that includes a two-layer structure wherein one layer is a biodegradable nonwoven material and the other material is a filled, biodegradable film. The biodegradable film is desirably filled with a material, such as a mineral, that imparts breathability to the film, and therefore to the laminate as a whole. As such, the overall laminate is highly breathable. Additionally, since the laminate includes two, biodegradable materials, the laminate is substantially biodegradable. As such, the laminate provides an environmentally friendly product that also performs as well or better than other conventional products.

The biodegradable, nonwoven material and the filled, biodegradable film are selected such that the resulting biodegradable/compostable laminate material is comprised of greater than 50%, by weight, of biodegradable polymers. As such, the resulting laminate will be biodegradable.

The laminate material of the present invention includes a first layer that is a biodegradable, nonwoven material. The biodegradable, nonwoven material is preferably comprised from a majority of biodegradable polymers. The biodegradable polymers may be selected from a variety of biodegradable polymers, organic and inorganic and may include, but are not limited to, aliphatic polyesters; polylactides (PLA); polyhydroxybutyrate-co-valerates (PHB-PHV); polycaprolactones (PCL); sulfonated polyethylene terephthalates; blends and mixtures thereof. Desirably, the present invention uses an aliphatic polyester polymer including, but not limited to, poly(lactic acid), polybutylene succinate and polybutylene succinate-co-adipate. More desirably, the present invention uses polybutylene succinate as one of the biodegradable polymers in the biodegradable, nonwoven material.

The biodegradable, nonwoven material utilizes the biodegradable polymer by forming fibers from the biodegradable polymer or polymers and then forming these fibers into the nonwoven material. As such, the biodegradable polymer is selected to have an appropriate viscosity range for fiber processing. This viscosity range will vary for each biodegradable polymer used in the biodegradable, nonwoven material.

Once the fibers are formed, they may be formed into the biodegradable, nonwoven material using a nonwoven process including, but not limited to, a spunbond process; a meltblown process; an airlaid process; or combinations thereof.

The laminate material of the present invention also includes a second layer that is a filled, biodegradable film. As with the biodegradable nonwoven, the biodegradable film includes a biodegradable polymer that may be made from a variety of biodegradable polymers, organic and inorganic. These polymers may include those set forth above that are utilized in the biodegradable, nonwoven material.

The filled, biodegradable film also includes a filler material. Suitable filler materials can be organic or inorganic, and are desirably in a form of individual, discreet particles. Suitable inorganic filler materials include metal oxides, metal hydroxides, metal carbonates, metal sulfates, various kinds of clay, silica, alumina, powdered metals, glass microspheres, or vugular void-containing particles. Particularly suitable filler materials include calcium carbonate, barium sulfate, sodium carbonate, magnesium carbonate, magnesium sulfate, barium carbonate, kaolin, carbon, calcium oxide, magnesium oxide, aluminum hydroxide, and titanium dioxide. Still other inorganic fillers can include those with particles having higher aspect ratios such as talc, mica and wollastonite. Suitable organic filler materials include, for example, latex particles, particles of thermoplastic elastomers, pulp powders, wood powders, cellulose derivatives, chitin, chitozan powder, powders of highly crystalline, high melting polymers, beads of highly crosslinked polymers, organosilicone powders, and powders of super absorbent polymers, such as partially neutralized polyacrylic acid, and the like, as well as combinations and derivatives thereof. These filler materials can improve toughness, softness, opacity, vapor transport rate (breathability), water dispersability, biodegradability, fluid immobilization and absorption, skin wellness, and other beneficial attributes of the film. Desirably, the filler is calcium carbonate.

The filler material is compounded into the biodegradable polymer base resin to create a microporous structure in the film. This microporous structure imparts breathability into the filled, biodegradable film. This breathability may be enhanced by stretching the film after the filler has been added to increase pore size.

To impart the microporous structure, the filler materials are desirably are particulates and range from about 0.1 to about 50 microns in size. More desirably, the filler particles have an average particle size of from about 1 micron to about 8 microns, and most desirably have an average particle size of about 1 micron.

The fillers may or may not be coated with a material to aid in processing. This materials may include, but are not limited to, stearic acid, behenic acid, or any other processing aid. Additionally, other additives may be included such as plasticizers, processing aids, rheology modifiers, antioxidants, UV light stabilizers, pigments, colorants, slip additives, antiblock agents, etc. which may be added before or after blending with the filler.

Desirably, the filled, biodegradable film contains from about 30 to about 100%, by weight, of biodegradable polymers; from about 70 to about 10%, by weight, of the orgainic or inorganic filler, and from about 0 to about 25%, by weight, of any additional additives.

The filled, biodegradable films may be made by compounding the filler and biodegradable polymers using an extrusion process and then converting these compounds into film. The film may be converted using a cast blown, blown film, or other applicable process. However, cast films are generally desired. These films may be embossed or not embossed. The films may be monolayer, or they may include coextruded films as long as each layer of the coextruded film is comprised from materials set forth above.

Once formed, these filled, biodegradable films will have a microporous structure that permits water vapor to pass through the film, thereby enhancing the breathability of the film, as compared to an unfilled film. However, these filled, biodegradable films may be stretched to enhance the breathability of the film. When stretched, the biodegradable polymer portions of the film slowly move away from the filler materials such that the micropores caused by the filler materials become larger, thereby increasing the amount of water vapor that may pass through the film, and therefore enhancing its breathability.

Stretching allows the filled, biodegradable films to have a desired breathability, water-dispersibility and/or thickness. The filled, biodegradable films may be subjected to a selected plurality of stretching operations, such as uniaxial stretching operation or biaxial stretching operation. Stretching operations can provide porous film with a distinctive porous morphology, can enhance water vapor transport through the film, and can improve water access, and enhance degradability of the film,. Preferably, the film is stretched from about 100 to about 500 percent of its original length. More preferably, the film is stretched from about 100 to about 300 percent of its original length.

The key parameters during stretching operations include stretching draw ratio, stretching strain rate, and stretching temperature. During the stretching operation, the filler-filled film may optionally be heated to provide a desired stretching effectiveness.

Stretching may be accomplished through a variety of different stretching processes, but the desired process is one in which the films are oriented only in the machine direction.

Desirably, a Machine Direction Orienter (MDO) is used. The MDO includes eight rolls, each of which may be heated and operated at different speeds. There are seven potential stretching areas, one between each set of rolls. The line speed, draw ratios between the rolls, and roll temperature can individually be adjusted to manipulate the pore structure and resulting properties of the films.

The factors used to determine the amount of stretching may include, but are not limited to, the amount of filler used, the desired water vapor transmission rate for the film, and the desired thickness of the final film. By using the filler and stretching, it is possible to create filled, biodegradable films having a water vapor transmission rate of at least about 3000 g/m$^2$/24 hours.

During stretching, the film sample may be optionally heated. In general, the stretching should be conducted at a temperature below the melting temperature of the biodegradable polymer. Excessively high temperature may reduce the generation of the desired micropores. Stretching at lower temperature may promote a more efficient debonding of filler particles during stretching and growth of the micropores.

After the biodegradable, nonwoven material and the filled, biodegradable film have been selected and formed, they are then laminated to form the laminates of the present invention. The laminates may be formed using a variety of laminating processes including, but not limited to, a thermal bonding process; an adhesive lamination process; or an extrusion lamination process. If an adhesive lamination process is selected, then the desired adhesive used would be a biodegradable adhesive.

The lamination process is selected to achieve the desired bonding requirements. Desirably, the lamination is achieved using a thermal bonding process. In such a process, the biodegradable, nonwoven material and the filled, biodegradable film are passed through a pressurized nip between two heated calendar rolls. Different thermal bonding configurations may be used as long as desired peel strength, hydrostatic pressure resistance, breathability and appearance criteria are satisfied. In general, these criteria are as follows: peel strength is desirably not lower than about 35 grams, as based on the STP 571W testing method. Hydrostatic pressure, desirably, is not lower than about 60 mba, as based on the RTM-4507 testing method. Breathability, as based on WVTR, is desirably not less than about 1000 g/m$^2$/24 hr, more desirably not less than about 2000 g/m$^2$/24, and most desirably not less than about 3000 g/m$^2$/24. For appearance, desirably, there are no visible holes or wrinkles.

The breathable, biodegradable/compostable laminate materials of the present invention may be used for a variety of different purposes. Desirably, the films are used in personal care products, such as diapers, feminine care articles, adult incontinence products, and training pants.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Examples 1–4

For the Examples contained herein, the following process conditions were used to form the films. A ZSK-30 co-rotating, twin screw extruder (manufactured by Werner & Pfleiderer) with 14 barrels and 1338 mm total processing section length was used. The first barrel was not heated but cooled by water. Dependent upon the composition being blended, the screw design of the extruder was modified accordingly. In some cases a ZSB-25 twin screw side feeder, also manufactured by Werner & Pfleiderer, was used to feed CaCO$_3$ filler into the extruder at barrel 8. Upon exit from the extruder, the polymer strands were solidified on either an air-cooled belt or a double belt cooler from Sandvik Process Systems. In either case, cooling was accomplished with a waterless system.

For film processing, a 36" film die with a 0.020" gap, EM50 silicon embossing roll with a water quench was used. This film setup was located at Huntsman Packaging in Newport News, Va. The extruder screw speed and wind-up speed were adjusted for each composition as necessary. The film processing conditions were monitored during the run: melt temperature, melt pressure, %torque, and qualitative observations.

For the Examples contained herein, the following process conditions were used to stretch the filled, biodegradable film portion of the breathable, biodegradable/compostable laminate material using a MDO:

TABLE 1

MDO Temperature Profile

| Roll 1 | Roll 2 | Roll 3 | Roll 4 | Roll 5 | Roll 6 | Roll 7 | Roll 8 |
|---|---|---|---|---|---|---|---|
| 120° F. | 150° F. | 150° F. | 150° F. | 150° F. | 70° F. | 70° F. | 150° F. |

TABLE 2

MDO Draw Ratios

Run Draw Ratios (%)

| Drive 1 | Drive 2 | Drive 3 | Drive 4 | Drive 5 | Drive 6 | Drive 7 | Overall Line Speed (ft/min) |
|---|---|---|---|---|---|---|---|
| 1 | 100 | 155 | 131 | 270 | 100 | 100 | 30 |

Upon exiting the MDO unit, the stretched film passed through a set of calendar rolls used to thermally bond the film to another substrate. A "baby objects" bond pattern was used. "Baby objects" is the bond pattern used in current HUGGIES® Supreme Diaper outer covers. A steel roll engraved with the baby objects pattern was placed on the top position of the calendar apparatus, and a non-patterned steel anvil roll was placed on the bottom. The temperature of the oil-heated calendar rolls could be adjusted individually. The spunbond was fed on to the topside the film web prior to the calendar rolls. The spunbond and the film were nipped between the heated rolls at operator specified pressures and were bonded.

The following laminates were formed. Examples 1–4 contain 49% calcium carbonate filled films that are laminated with different basis weights of BAU spunbond. The films include polybutylene succinate adipate copolymers (PBSA). A PBSA, available from Showa Highpolymer Co., Ltd., Tokyo, Japan, under the designation BIONOLLE® 3001 PBSA, was obtained. The nonwovens comprise 41.7% BIONOLLE® 1020 polybutylene succinate polymer (PBS), 41.7% BIONOLLE® 3020 polybutylene succinate-co-adipate polymer (PBSA), 14.7% adipic acid; and 2% of a material used as a wetting agent that was obtained from Petrolite Corporation of Tulsa, Oklahoma, under the designation UNITHOX™ 480 ethoxylated alcohol. For the remainder of these Examples, this nonwoven material will be referred to under the abbreviation "BAU".

Examples A–D are comparative examples. Example A uses the same non-woven as Example 1, but the film is 100% Bionelle 3001. Example B is a Breathable Stretch Thermal Laminate (BSTL) outer cover from a HUGGIES® diaper. A Highly Breathable Outer cover was used in Example C. Finally, Example D contains a polyvinyl alcohol (PVOH) film. However, the film could not be converted acceptably and, as such, no additional information is provided.

TABLE 3

| | Examples | | | | | | |
|---|---|---|---|---|---|---|---|
| | | Film Description | | | | Nonwoven Description | |
| Example | Polymer | Filler (wt %) | Pre-Stretch Thickness (mil) | Pre-Stretch Width (in) | Composition | Basis Weight (osy) | Width (in) |
| 1 | Bionolle 3001 | 49 | 2.1 | 17 | BAU | 0.9 | 20 |
| 2 | Bionolle 3001 | 49 | 2.1 | 13 | BAU | 0.75 | 14 |
| 3 | Bionolle 3001 | 49 | 2.1 | 13 | BAU | 0.9 | 14 |
| 4 | Bionolle 3001 | 49 | 2.1 | 13 | BAU | 1.2 | 14 |
| A | Bionolle 3001 | 0 | 1.8 | 17 | BAU | 0.9 | 20 |
| B | K-C Huntsman | 50 | N/A | N/A | PP | 0.7 | N/A |
| C | K-C Huntsman | 58 | N/A | N/A | PP | 0.6 | N/A |
| D | PVOH | N/A | N/A | N/A | N/A | N/A | N/A |

The films were then evaluated based upon the following parameters: Processability; Water Vapor Transmission Rate (WVTR) and Degradability. The results for each laminate are set forth in Table 4.

TABLE 4

| | | Physical Properties | |
|---|---|---|---|
| Example | Process-ability | WVTR g/m²/24 hr | Degradability |
| 1 | Good | 3250 | >70 wt % biodegradable; >15% inert |
| 2 | Good | 3300 | >65 wt % biodegradable; >20% inert |
| 3 | Good | 3140 | >70 wt % biodegradable; >15% inert |
| 4 | Good | 3960 | >70 wt % biodegradable; >15% inert |
| A | Good | 1350 | >85 wt % biodegradable |
| B | Good | 4100 | Not degradable |
| C | Good | 1500 | Not degradable |
| D | Poor | N/A | N/A |

The processability of each composition was assessed on a qualitative basis. Compositions were deemed to have good processability if they could be compounded, cast into films, stretched and laminated without an unusual level of difficulty.

Examples 1–4 and comparative examples A–C had good processability. Comparative example D had poor processability. Specifically, this composition could not be cast into a reasonably thin film. The films that were obtained were brittle and contained gels. It was determined that PVOH was not an applicable biodegradable polymer for use in the present invention.

The breathability of the samples was assessed according to the following test method. A 3-inch diameter test specimen was sealed over a cup containing water and placed in an oven for 24 hours. The weight of the cup assembly was measured before and after the 24 hour time period. The weight lost was equivalent to amount of moisture that traveled through the test material. The WVTR value for the material is calculated from this information. Cup testing is only effective at WVTR values <5,000 g/m²/24 hr.

Current BSTL outer covers have a WVTR value of about 1500 g/m²/24 hr, while next generation highly breathable outer covers target a WVTR of about 3800 g/m²/24 hr. It was found that all of the Examples of the present invention had WVTR values that were higher than current BSTL film. Specifically, values ranged from 3140 to 3960 g/m²/24 hr.

Comparative example A had a breathability of 1350 g/m²/24 hr. This film contained BIONOLLE® polymer, but no filler, and therefore a porous structure was not created during the film stretching step. The breathability that was measured was due to the inherently breathable nature of the BIONOLLE® material. This built-in breathability gives the biodegradable outer covers an edge over polyolefin outer covers, which are only breathable when filled and stretched.

Degradability was determined using ASTM Test Method 5338.92. A material is biodegradable if it degrades from the action of naturally occurring microorganisms, such as bacteria, fungi or algae. In the present Examples, more than 50% of each material had to include biodegradable materials to satisfy degradability. Current European regulations state that a material is to be considered biodegradable if a minimum of 90% of the material (by weight) or 60% of each organic component biodegrades within 6 months. In addition, no more than 50 wt % of the product composition can be comprised of inorganic compounds.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A breathable, biodegradable/compostable laminate material comprising:
   a. a biodegradable nonwoven material selected from the group comprising aliphatic polyesters; polylactides; polyhydroxybutyrate-co-valerates; sulfonated polyethylene terephthalates; blends or mixtures thereof; and
   b. a filled, biodegradable film stretched from about 100 to about 500 percent of its original length and selected from the group consisting of aliphatic polyesters; polylactides; polyhydroxybutyrate-co-valerates; sulfonated polyethylene terephthalates; and blends or mixtures thereof;
   wherein the breathable, biodegradable/compostable laminate material has a water vapor transmission rate that is greater than about 3000 g/m²/24 hr.

2. The breathable, biodegradable/compostable laminate material of claim 1, wherein the biodegradable nonwoven material comprises polybutylene succinate.

3. The breathable, biodegradable/compostable laminate material of claim 1, wherein the filled, biodegradable film includes a filler selected from clay, silica, alumina, powdered metals, glass microspheres, calcium carbonate, barium sulfate, sodium carbonate, magnesium carbonate, magnesium sulfate, barium carbonate, kaolin, carbon, calcium oxide, magnesium oxide, aluminum hydroxide, titanium dioxide, talc, mica, wollastonite, latex particles, particles of thermoplastic elastomers, pulp powders, wood powders, cellulose derivatives, chitin, chitozan powder, organosilicone powders, polyacrylic acid, magnesium sulfate, sodium sulfite, sodium hydrogen sulfite, sodium sulfate, sodium hydrogen sulfate, sodium phosphate, sodium hydrogen phosphate, sodium carbonate, sodium hydrogen carbonate, potassium carbonate, sodium hydroxide, potassium hydroxide, sodium chloride, potassium chloride, or mixtures thereof.

4. The breathable, biodegradable/compostable laminate material of claim 2, wherein the filler comprises calcium carbonate.

5. The breathable, biodegradable/compostable laminate material of claim 1, wherein a filler comprises from about 10 to about 70 percent by weight of the filled, biodegradable film.

6. The breathable, biodegradable/compostable laminate material of claim 4, wherein the filler comprises from about 30 to about 60 percent by weight of the filled, biodegradable film.

7. A method of making a breathable, biodegradable/compostable laminate material comprising:
   stretching a filled, biodegradable film to form the breathable, biodegradable/compostable laminate material from about 100 to about 500 percent of its original length; and,
   subsequently laminating a biodegradable nonwoven material selected from the group consisting of aliphatic polyesters; polylactides; polyhydroxybutyrate-co-valerates; sulfonated polyethylene terephthalates; and blends or mixtures thereof and the filled, biodegradable film to form the breathable, biodegradable/compostable laminate material;
   wherein the breathable, biodegradable/compostable laminate material has a water vapor transmission rate that is greater than about 3000 g/m²/24 hr.

8. The method of claim 7, wherein the biodegradable nonwoven material comprises polybutylene succinate.

9. The method of claim 7, wherein the filled, biodegradable film includes aliphatic polyesters; polylactides; polyhydroxybutyrate-co-valerates; polycaprolactones; sulfonated polyethylene terephthalates; blends or mixtures thereof.

10. The method of claim 7, wherein the filled, biodegradable film includes a filler selected from clay, silica, alumina, powdered metals, glass microspheres, calcium carbonate, barium sulfate, sodium carbonate, magnesium carbonate, magnesium sulfate, barium carbonate, kaolin, carbon, calcium oxide, magnesium oxide, aluminum hydroxide, titanium dioxide, talc, mica, wollastonite, latex particles, particles of thermoplastic elastomers, pulp powders, wood powders, cellulose derivatives, chitin, chitozan powder, organosilicone powders, polyacrylic acid, magnesium sulfate, sodium sulfite, sodium hydrogen sulfite, sodium sulfate, sodium hydrogen sulfate, sodium phosphate, sodium hydrogen phosphate, sodium carbonate, sodium hydrogen carbonate, potassium carbonate, sodium hydroxide, potassium hydroxide, sodium chloride, potassium chloride, or mixtures thereof.

11. The method of claim 8, wherein the filler comprises calcium carbonate.

12. The method of claim 7, further comprising a filler in an amount from about 10 to about 70 percent by weight of the filled, biodegradable film.

13. The method of claim 11, wherein the filler comprises from about 30 to about 60 percent by weight of the filled, biodegradable film.

14. The method of claim 7, wherein the biodegradable nonwoven material and the filled, biodegradable film are laminated using a thermal bonding process.

* * * * *